United States Patent
West et al.

(10) Patent No.: US 10,261,097 B2
(45) Date of Patent: Apr. 16, 2019

(54) METHODS FOR THE DIAGNOSIS AND TREATMENT OF NEUROLOGICAL AND NEURODEGENERATIVE DISEASES, DISORDERS AND ASSOCIATED PROCESSES

(71) Applicant: C2N Diagnostics, Saint Louis, MO (US)

(72) Inventors: Tim West, Saint Louis, MO (US); Andrew C. Paoletti, Saint Louis, MO (US)

(73) Assignee: C2N Diagnostics, St. Louis, MO (US)

( * ) Notice: Subject to any disclaimer, the term of this patent is extended or adjusted under 35 U.S.C. 154(b) by 0 days.

(21) Appl. No.: 15/178,419

(22) Filed: Jun. 9, 2016

(65) Prior Publication Data
US 2016/0313353 A1 Oct. 27, 2016

Related U.S. Application Data

(63) Continuation of application No. 14/345,390, filed as application No. PCT/US2012/056144 on Sep. 19, 2012, now abandoned.

(60) Provisional application No. 61/536,300, filed on Sep. 19, 2011.

(51) Int. Cl.
| | |
|---|---|
| *G01N 33/569* | (2006.01) |
| *G01N 33/53* | (2006.01) |
| *G01N 33/566* | (2006.01) |
| *G01N 33/567* | (2006.01) |
| *G01N 33/68* | (2006.01) |

(52) U.S. Cl.
CPC ..... *G01N 33/6896* (2013.01); *G01N 2333/47* (2013.01); *G01N 2500/04* (2013.01); *G01N 2800/28* (2013.01); *G01N 2800/2821* (2013.01); *G01N 2800/2835* (2013.01); *G01N 2800/2871* (2013.01); *G01N 2800/52* (2013.01)

(58) Field of Classification Search
None
See application file for complete search history.

(56) References Cited

U.S. PATENT DOCUMENTS

| | | |
|---|---|---|
| 8,232,107 B2 | 7/2012 | Bateman |
| 2010/0120056 A1 | 5/2010 | Bar-Or |
| 2010/0145194 A1 | 6/2010 | Joshi et al. |
| 2011/0111511 A1 | 5/2011 | Bateman et al. |
| 2011/0159527 A1 | 6/2011 | Schlossmacher et al. |
| 2011/0207796 A1 | 8/2011 | Anderson et al. |

FOREIGN PATENT DOCUMENTS

| | | |
|---|---|---|
| WO | WO 2003/061479 A1 | 7/2003 |
| WO | WO 2006/107814 A2 | 10/2006 |
| WO | WO 2007/075923 A2 | 7/2007 |
| WO | WO 2010/065878 A1 | 6/2010 |

OTHER PUBLICATIONS

Extended European Search Report dated Mar. 26, 2015, regarding EP 12 83 3356.
Japanese Office Action dated Jul. 27, 2016, regarding JP 2014-530960.
European Office Action dated Oct. 4, 2017, regarding EP 12 83 3356.4.
Visanji, Naomi P. et al.: "*The Systemic Synuclein Sampling Study: toward a biomarker for Parkinson's disease*"; Biomarkers in Medicine, vol. 11, No. 4, Apr. 2017, pp. 359-368.
Japanese Decision to Grant issued on Jun. 18, 2018, regarding JP 2014-530960 (with English translation).

*Primary Examiner* — Olga N Chernyshev
(74) *Attorney, Agent, or Firm* — DLA Piper LLP (US)

(57) ABSTRACT

The invention generally relates to methods for the diagnosis and treatment of neurological and neurodegenerative diseases, disorders, and associated processes. Specifically, the present invention is directed toward methods to determine prognosis, diagnosis or efficacy of a therapeutic regimen by using a detectable label to measure levels of alpha-synuclein.

12 Claims, 10 Drawing Sheets

Specification includes a Sequence Listing.

```
CLUSTAL 2.0.10 multiple sequence alignment

↓   ↓                                 ↓
alpha     MDVFMKGLSKAKEGVVAAAEKTKQGVAEAAGKTKEGVLYVGSKTKEGVVQGVAQVAEKTK 60
beta      MDVFMKGLSMAKEGVVAAAEKTKQGVTEAAEKTKEGVLYVGSKTPEGVVQGVAQVAEKTK 60
gamma     MDVFMKGFSIAKEGVVGAVEKTKQGVTEAAEKTKEGVMYVGAKTKENVVQSVTSVAEKTK 60
          ****  **:*  ******.*.*******:***  ******:***:**:*  **:.:.:******

↓   ↓                               ↓
alpha     EQVTNVGGAVVTGVTAVAQKTVEGAGSIAAATGFVKKDQLG---KNEEGAPQ--EGILED 115
beta      EQASHLGGAVFS-----------GAGNIAAATGLVKREEFPTDLKPEEVAQEAAEEPLIE 109
gamma     EQANAVSEAVVSSVNTVATKTVEEAENIAVTSGVVRKEDLR------PSAFQ------QE 108
          **:.  . **.:           *  .**::*.*.*::::         *  :         :

alpha     MPVDPDNEAYEMPSEEGYQDYEPEA 140
beta      PLMEPEGESYEDPPQEEYQEYEPEA 134
gamma     GVASKEKEEVAEEAQSGGD------ 127
            . : *    .:. :
```

FIG. 2

| Start | Peptide Sequence | End |
|---|---|---|
| 11 | AKEGVVAAAEKTK | 23 |
| 11 | AKEGVVAAAEK | 21 |
| 33 | TKEGVLYVGSK | 43 |
| 35 | EGVLYVGSK | 43 |
| 44 | TKEGVVHGVATVAEK | 58 |
| 46 | EGVVHGVATVAEK | 58 |
| 59 | TKEQVTNVGGAVVTGVTAVAQK | 80 |
| 61 | EQVTNVGGAVVTGVTAVAQK | 80 |
| 81 | TVEGAGSIAAATGFVKK | 97 |
| 81 | TVEGAGSIAAATGFVK | 96 |

FIG. 3

SEQUENCE LISTING

```
<160> NUMBER OF SEQ ID NOS: 13

<210> SEQ ID NO 1
<211> LENGTH: 140
<212> TYPE: PRT
<213> ORGANISM: Homo sapiens

<400> SEQUENCE: 1

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
    130                 135                 140

<210> SEQ ID NO 2
<211> LENGTH: 134
<212> TYPE: PRT
<213> ORGANISM: Homo sapiens

<400> SEQUENCE: 2

Met Asp Val Phe Met Lys Gly Leu Ser Met Ala Lys Glu Gly Val Val
1               5                   10                  15

Ala Ala Ala Glu Lys Thr Lys Gln Gly Val Thr Glu Ala Ala Glu Lys
            20                  25                  30

Thr Lys Glu Gly Val Leu Tyr Val Gly Ser Lys Thr Arg Glu Gly Val
        35                  40                  45
```

```
Val Gln Gly Val Ala Ser Val Ala Glu Lys Thr Lys Glu Gln Ala Ser
    50                  55                  60
His Leu Gly Gly Ala Val Phe Ser Gly Ala Gly Asn Ile Ala Ala Ala
65                  70                  75                  80
Thr Gly Leu Val Lys Arg Glu Glu Phe Pro Thr Asp Leu Lys Pro Glu
                85                  90                  95
Glu Val Ala Gln Glu Ala Ala Glu Glu Pro Leu Ile Glu Pro Leu Met
            100                 105                 110
Glu Pro Glu Gly Glu Ser Tyr Glu Asp Pro Pro Gln Glu Glu Tyr Gln
        115                 120                 125
Glu Tyr Glu Pro Glu Ala
    130

<210> SEQ ID NO 3
<211> LENGTH: 127
<212> TYPE: PRT
<213> ORGANISM: Homo sapiens

<400> SEQUENCE: 3

Met Asp Val Phe Lys Lys Gly Phe Ser Ile Ala Lys Glu Gly Val Val
1               5                   10                  15
Gly Ala Val Glu Lys Thr Lys Gln Gly Val Thr Glu Ala Ala Glu Lys
            20                  25                  30
Thr Lys Glu Gly Val Met Tyr Val Gly Ala Lys Thr Lys Glu Asn Val
        35                  40                  45
Val Gln Ser Val Thr Ser Val Ala Glu Lys Thr Lys Glu Gln Ala Asn
    50                  55                  60
Ala Val Ser Glu Ala Val Val Ser Ser Val Asn Thr Val Ala Thr Lys
65                  70                  75                  80
Thr Val Glu Glu Ala Glu Asn Ile Ala Val Thr Ser Gly Val Val Arg
                85                  90                  95
Lys Glu Asp Leu Arg Pro Ser Ala Pro Gln Gln Glu Gly Val Ala Ser
            100                 105                 110
Lys Glu Lys Glu Glu Val Ala Glu Glu Ala Gln Ser Gly Gly Asp
        115                 120                 125

<210> SEQ ID NO 4
<211> LENGTH: 13
<212> TYPE: PRT
<213> ORGANISM: Homo sapiens

<400> SEQUENCE: 4

Ala Lys Glu Gly Val Val Ala Ala Ala Glu Lys Thr Lys
1               5                   10

<210> SEQ ID NO 5
<211> LENGTH: 11
<212> TYPE: PRT
<213> ORGANISM: Homo sapiens

<400> SEQUENCE: 5

Ala Lys Glu Gly Val Val Ala Ala Ala Glu Lys
1               5                   10

<210> SEQ ID NO 6
<211> LENGTH: 11
<212> TYPE: PRT
<213> ORGANISM: Homo sapiens
```

```
<400> SEQUENCE: 6

Thr Lys Glu Gly Val Leu Tyr Val Gly Ser Lys
1               5                   10

<210> SEQ ID NO 7
<211> LENGTH: 9
<212> TYPE: PRT
<213> ORGANISM: Homo sapiens

<400> SEQUENCE: 7

Glu Gly Val Leu Tyr Val Gly Ser Lys
1               5

<210> SEQ ID NO 8
<211> LENGTH: 15
<212> TYPE: PRT
<213> ORGANISM: Homo sapiens

<400> SEQUENCE: 8

Thr Lys Glu Gly Val Val His Gly Val Ala Thr Val Ala Glu Lys
1               5                   10                  15

<210> SEQ ID NO 9
<211> LENGTH: 13
<212> TYPE: PRT
<213> ORGANISM: Homo sapiens

<400> SEQUENCE: 9

Glu Gly Val Val His Gly Val Ala Thr Val Ala Glu Lys
1               5                   10

<210> SEQ ID NO 10
<211> LENGTH: 22
<212> TYPE: PRT
<213> ORGANISM: Homo sapiens

<400> SEQUENCE: 10

Thr Lys Glu Gln Val Thr Asn Val Gly Gly Ala Val Val Thr Gly Val
1               5                   10                  15

Thr Ala Val Ala Gln Lys
            20

<210> SEQ ID NO 11
<211> LENGTH: 20
<212> TYPE: PRT
<213> ORGANISM: Homo sapiens

<400> SEQUENCE: 11

Glu Gln Val Thr Asn Val Gly Gly Ala Val Val Thr Gly Val Thr Ala
1               5                   10                  15

Val Ala Gln Lys
            20

<210> SEQ ID NO 12
<211> LENGTH: 17
<212> TYPE: PRT
<213> ORGANISM: Homo sapiens

<400> SEQUENCE: 12

Thr Val Glu Gly Ala Gly Ser Ile Ala Ala Ala Thr Gly Phe Val Lys
1               5                   10                  15

Lys
```

```
<210> SEQ ID NO 13
<211> LENGTH: 16
<212> TYPE: PRT
<213> ORGANISM: Homo sapiens

<400> SEQUENCE: 13

Thr Val Glu Gly Ala Gly Ser Ile Ala Ala Ala Thr Gly Phe Val Lys
1               5                  10                  15
```

METHODS FOR THE DIAGNOSIS AND TREATMENT OF NEUROLOGICAL AND NEURODEGENERATIVE DISEASES, DISORDERS AND ASSOCIATED PROCESSES

CROSS-REFERENCE TO RELATED APPLICATIONS

This application is a continuation application of U.S. application Ser. No. 14/345,390 filed Mar. 17, 2014, which claims the benefit under 35 USC § 371 National Stage application of International Application No. PCT/US12/56144 filed Sep. 19, 2012; which claims the benefit under 35 USC § 119(e) to U.S. Application Ser. No. 61/536,300 filed Sep. 19, 2011. The disclosure of each of the prior applications is considered part of and is incorporated by reference in the disclosure of this application.

BACKGROUND OF THE INVENTION

Field of the Invention

The invention generally relates to methods for the diagnosis and treatment of neurological and neurodegenerative diseases, disorders, and associated processes, and more specifically, to levels of alpha synuclein and correlation with disease.

Background Information

The protein alpha-synuclein has been implicated in Parkinson's Disease (PD) through a variety of human and animal studies. Recent studies have shown that the CSF concentration of alpha-synuclein is significantly lower in patients with PD than in control subjects, suggesting that the metabolism of alpha-synuclein is altered in patients with PD. Like other protein misfolding diseases, protein misfolding is concentration-dependent. Thus, decreasing synthesis or increasing clearance of synuclein is a potential way to develop treatments for PD and drug companies have focused on the metabolism of this protein as a drug target.

The stable isotope labeling kinetic (SILK) assay relies on the ability to detect metabolic incorporation of stable isotope labeled amino acids into proteins and peptides. Stable isotopes add a small amount of weight (2-100 Daltons) to peptides containing the stable isotope and this additional weight can be measured by a mass spectrometer. By measuring metabolic incorporation of stable isotopes into proteins in the CSF at various times after administration of a stable isotope, the SILK assay can be used to measure production and clearance of proteins in the human central nervous system.

The following describes the protocol for measuring the metabolism of brain derived alpha-synuclein in a human subject. A study participant is identified and enrolled in the study. On the first day of the study the participant will have IV and lumbar catheters placed and will be administered a stable isotope for a pre-determined amount of time. Samples of plasma and CSF will be drawn through the catheters at pre-determined times. Alpha-synuclein will then be isolated from the biological samples and the incorporation of the stable isotope into the protein will be measured by a mass spectrometer. The change in labeled to unlabeled alpha-synuclein over time will allow for calculation of production and clearance rates for the protein.

Measuring alpha-synuclein metabolism can provide results to inform about synthesis and clearance rates of alpha-synuclein in normal as well as disease states, as well as provide a method to directly determine the effects in humans of treatments which target alpha-synuclein synthesis and clearance.

SUMMARY OF THE INVENTION

In one embodiment of the invention, we describe the methods by which alpha-synuclein is isolated from biological samples by immunoprecipitation using an antibody that recognizes alpha-synuclein. In this embodiment, the isolated protein is eluted from the antibody, for example by using formic acid and then digested with trypsin or another protease. Incorporation of stable isotopes into alpha-synuclein peptides is then analyzed on a mass spectrometer and a ratio of labeled to unlabeled alpha-synuclein is calculated.

In one embodiment, the present invention is a method to determine prognosis, diagnosis or efficacy of a therapeutic regimen in a subject comprising contacting a biological sample from a subject with a detectable isotope to detect the level of alpha-synuclein in the sample.

In an embodiment, the present invention is a method to diagnose an alpha-synuclein related disease or disorder comprising: (a) administration of a labeled moiety to a subject suspected of having an alpha-synuclein related disease or disorder; (b) collection of a biological sample from the subject and a corresponding normal sample; (c) measurement of labeled alpha-synuclein and unlabeled alpha-synuclein from the subject and corresponding normal sample; (d) determination of the ratio of labeled alpha-synuclein to unlabeled alpha-synuclein from the subject and corresponding normal sample; (e) determination of alpha-synuclein metabolism from the ratios of step (d); and (f) comparison of the alpha-synuclein metabolism from the subject to the alpha-synuclein metabolism from the corresponding normal sample, wherein a change in the alpha-synuclein metabolism of the subject compared to the corresponding normal sample is indicative of positive diagnosis of an alpha-synuclein related disease or disorder, thereby diagnosing an alpha-synuclein related disease or disorder.

In another embodiment, the present invention is a method to determine the prognosis an alpha-synuclein related disease or disorder comprising: (a) administration of a labeled moiety to a subject suspected of having an alpha-synuclein related disease or disorder; (b) collection of a biological sample from the subject and a corresponding normal sample; (c) measurement of labeled alpha-synuclein and unlabeled alpha-synuclein from the subject and corresponding normal sample; (d) determination of the ratio of labeled alpha-synuclein to unlabeled alpha-synuclein from the subject and corresponding normal sample; (e) determination of alpha-synuclein metabolism from the ratios of step (d); and (f) comparison of the alpha-synuclein metabolism from the subject to the alpha-synuclein metabolism from the corresponding normal sample, wherein a change in the alpha-synuclein metabolism of the subject compared to the corresponding normal sample is indicative of positive prognosis of an alpha-synuclein related disease or disorder, thereby prognosing an alpha-synuclein related disease or disorder.

In an additional embodiment, the present invention is a method to determine the efficacy of a therapeutic regimen to treat an alpha-synuclein related disease or disorder comprising: (a) administration of a labeled moiety and a therapeutic agent to a subject suspected of having an alpha-synuclein related disease or disorder; (b) collection of a biological sample from the subject and a corresponding normal sample; (c) measurement of labeled alpha-synuclein and unlabeled alpha-synuclein from the subject and corresponding normal sample; (d) determination of the ratio of labeled alpha-synuclein to unlabeled alpha-synuclein from the subject and corresponding normal sample; and (e) determination of alpha-synuclein metabolism from the ratios of step (d); (f) comparison of the alpha-synuclein metabolism from the subject to the alpha-synuclein metabolism from the corresponding normal sample, wherein a change in the alpha-synuclein metabolism of the subject compared to the corresponding normal sample is indicative of efficacy of a therapeutic regimen of a therapeutic agent to treat an alpha-synuclein related disease or disorder, thereby determining the efficacy of a therapeutic regimen to treat an alpha-synuclein related disease or disorder.

In an embodiment, the present invention is an in vivo method to identify a therapeutic agent to treat an alpha-synuclein related disease or disorder comprising: (a) administration of a labeled moiety and a therapeutic agent to a subject suspected of having an alpha-synuclein related disease or disorder; (b) collection of a biological sample from the subject and a corresponding normal sample; (c) measurement of labeled alpha-synuclein and unlabeled alpha-synuclein from the subject and corresponding normal sample; (d) determination of the ratio of labeled alpha-synuclein to unlabeled alpha-synuclein from the subject and corresponding normal sample; (e) determination of alpha-synuclein metabolism from the ratios of step (d); and (f) comparison of the alpha-synuclein metabolism from the subject to the alpha-synuclein metabolism from the corresponding normal sample, wherein a change in alpha-synuclein metabolism of the subject compared to the corresponding normal sample is indicative of the identification of a therapeutic agent to treat an alpha-synuclein related disease or disorder, thereby identifying a therapeutic agent to treat an alpha-synuclein related disease or disorder.

In one embodiment, the present invention is an in vitro method to identify a therapeutic agent to treat an alpha-synuclein related disease or disorder comprising: (a) administration of a labeled moiety and a therapeutic agent to cells; (b) collection of alpha-synuclein from the cells and a corresponding normal sample; (c) measurement of labeled alpha-synuclein and unlabeled alpha-synuclein from the cells and corresponding normal sample; (d) determination of the ratio of labeled alpha-synuclein to unlabeled alpha-synuclein from the cells and corresponding normal sample; (e) determination of alpha-synuclein metabolism from the ratios of step (d); and (f) comparison of the alpha-synuclein metabolism from the cells to the alpha-synuclein metabolism from the corresponding normal sample, wherein a change in alpha-synuclein metabolism of the cells compared to the corresponding normal sample is indicative of the identification of a therapeutic agent to treat an alpha-synuclein related disease or disorder, thereby identifying a therapeutic agent to treat an alpha-synuclein related disease or disorder an alpha-synuclein related disease or disorder.

In one embodiment, the present invention is a method to predict subject response to a therapeutic agent to treat an alpha-synuclein related disease or disorder comprising: (a) administration of a labeled moiety and a therapeutic agent to a subject suspected of having an alpha-synuclein related disease or disorder; (b) collection of a biological sample from the subject and a corresponding normal sample; (c) measurement of labeled alpha-synuclein and unlabeled alpha-synuclein from the subject and corresponding normal sample; (d) determination of the ratio of labeled alpha-synuclein to unlabeled alpha-synuclein from the subject and corresponding normal sample; (e) determination of alpha-synuclein metabolism from the ratios of step (d); and (f) comparison of the alpha-synuclein metabolism from the subject to the alpha-synuclein metabolism from the corresponding normal sample, wherein a change in the alpha-synuclein metabolism of the subject compared to the corresponding normal sample is indicative of the identification of a therapeutic agent to treat an alpha-synuclein related disease or disorder, thereby diagnosing an alpha-synuclein related disease or disorder.

In one aspect, the labeled moiety is a labeled amino acid. In a further aspect, the amino acid is labeled with a radioisotope or a non-radio labeled isotope. In one aspect, the amino acid is labeled with a non-radio labeled isotope. In an additional aspect, the non-radio labeled isotope can be $^2$H, $^{13}$C, $^{15}$N, $^{17}$ or $^{18}$O and $^{33,\ 34\ or\ 36}$S. In a further aspect, the amino acid can be leucine, isoleucine and phenylalanine. Further, the labeled amino acid maybe one or more of $^{15}$N$_x$ labeled leucine, wherein x=1-6; $^{13}$C$_x$ labeled phenylalanine, wherein x=1-9 and $^{13}$C$_x$ labeled isoleucine, wherein x=1-6. In one aspect, the labeled moiety is labeled water. In a further aspect, the labeled water is deuterated water ($^2$H$_2$O), oxygen 18 water (H$_2$$^{18}$O) or other similar molecules. In one aspect, the biological sample is a bodily fluid or a tissue sample. In a further aspect, the bodily fluid can be blood, plasma, blood serum, cerebral spinal fluid (CSF), urine, saliva, perspiration and tears. In one aspect, the bodily fluid is CSF. In an additional aspect, the tissue sample is a CNS sample. In a further aspect, the CNS sample can be tissue from the CNS system, brain tissue, the forebrain tissue, the interbrain tissue, the midbrain tissue, the hindbrain tissue and the spinal cord tissue.

In one aspect the therapeutic agent can be small molecule inhibitors of alpha-synuclein, antibodies against alpha-synuclein, alpha-synuclein clearance activators, sirtuin 2 inhibitors, proteomsome inhibitors, small molecule inhibitors of alpha-synuclein polymerization, L-DOPA, cholesterylester transfer protein (CEPT) inhibitors, metalloprotease inhibitors, cholinesterase inhibitors, NMDA receptor antagonists, hormones, neuroprotective agents and cell death inhibitors. In one aspect, the therapeutic agent is L-DOPA.

In one embodiment, the present invention is a kit for determine prognosis, diagnosis or efficacy of a therapeutic regimen in a subject having or suspected of having an alpha-synuclein related disease or disorder. In one aspect, the kit comprises one or more labeled moieties and a means for administering the one or more moieties to a subject. In an additional aspect, the kit further comprises a means for obtaining a biological sample and instructions for determining the ratio of labeled to unlabeled alpha-synuclein.

BRIEF DESCRIPTION OF THE DRAWINGS

FIG. 2 shows a multiple sequence comparison (SEQ ID NOs:1-3) showing differences in the amino acid sequence of alpha-, beta- and gamma-synuclein.

FIG. 3 shows tryptic peptides originating from alpha-synuclein (SEQ ID NOs:4-13) observed on the mass spectrometer. We have analyzed alpha-synuclein isolated from biological sources such as cerebrospinal fluid, conditioned cell culture media, and cell lysates as well as recombinant alpha-synuclein.

DETAILED DESCRIPTION OF THE INVENTION

Figure 1:
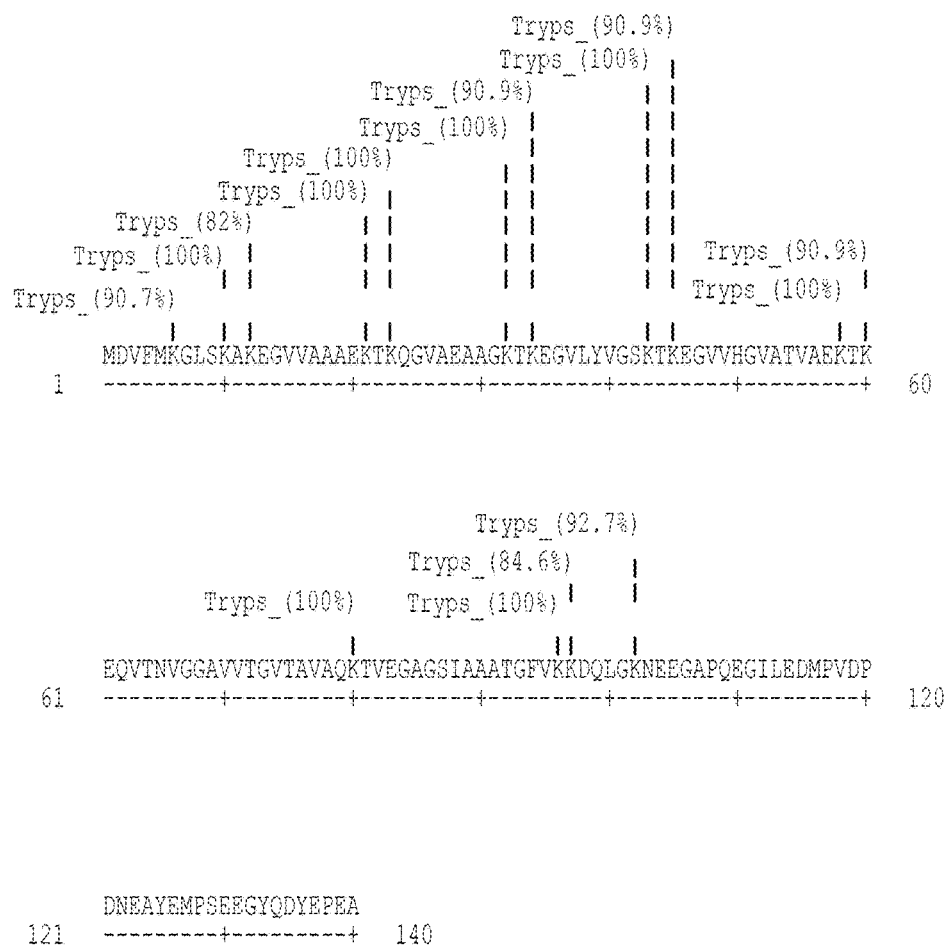
FIG. 1 shows the amino acid sequence of alpha-synuclein (SEQ ID NO:1) showing the tryptic cleavage sites.
Figure 4:
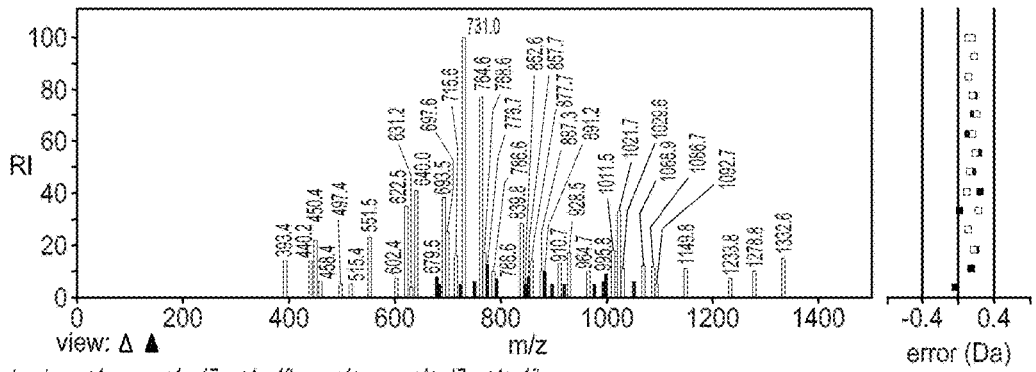
FIG. 4 shows the mass spectrum of alpha-synuclein 81-96 peptide (SEQ ID NO:13). Contains essential amino acid phenylalanine (F). The presence of a phenylalanine in the 81-96 tryptic peptide makes this peptide a peptide that can be used to monitor metabolism of alpha-synuclein by administration of stable isotope labeled phenylalanine.
Figure 5:
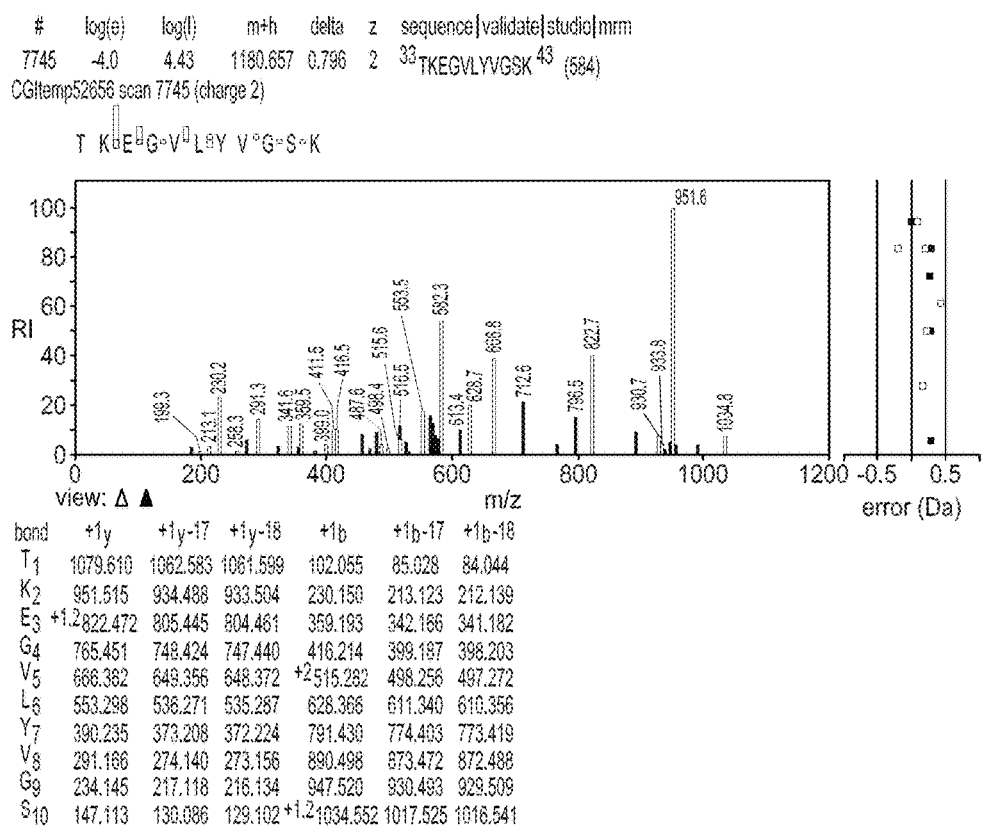
FIG. 5 shows the mass spectrum of alpha-synuclein 33-43 peptide (SEQ ID NO:6). Contains essential amino acid leucine (L). The presence of a leucine in the 33-43 tryptic peptide makes this peptide a peptide that can be used to monitor metabolism of alpha-synuclein by administration of stable isotope labeled leucine.
Figure 6:
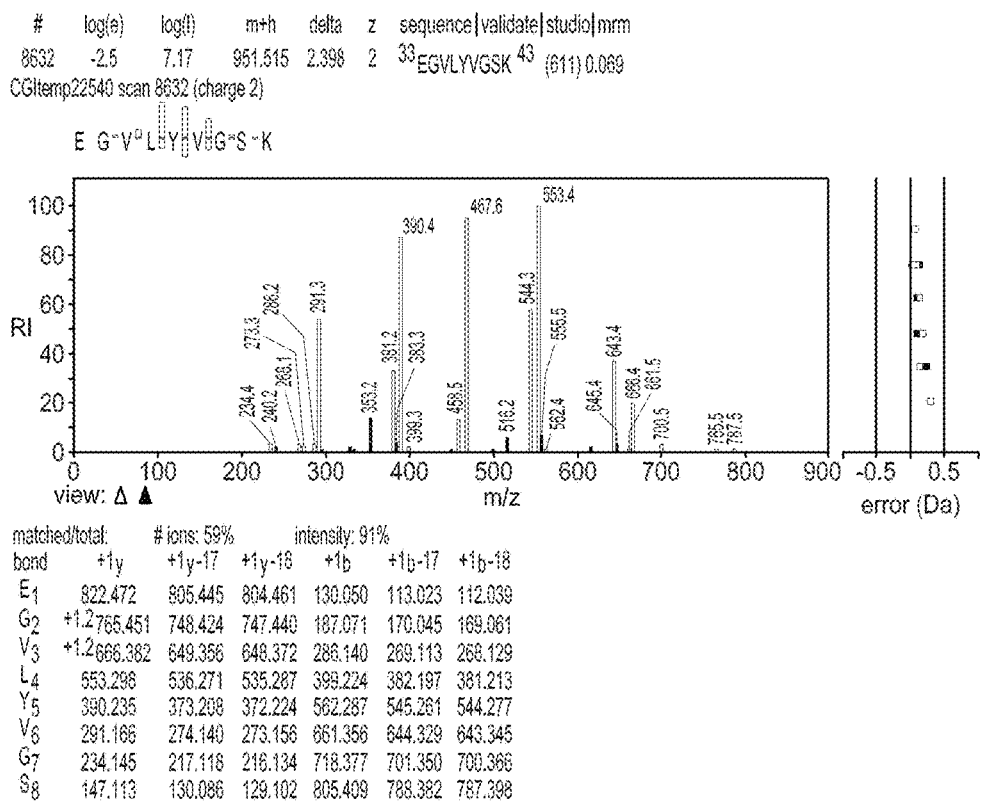
FIG. 6 shows the mass spectrum of alpha-synuclein 35-43 peptide (SEQ ID NO:7). Contains essential amino acid leucine (L). The presence of a leucine in the 35-43 tryptic peptide makes this peptide a peptide that can be used to monitor metabolism of alpha-synuclein by administration of stable isotope labeled leucine.
Figure 7:
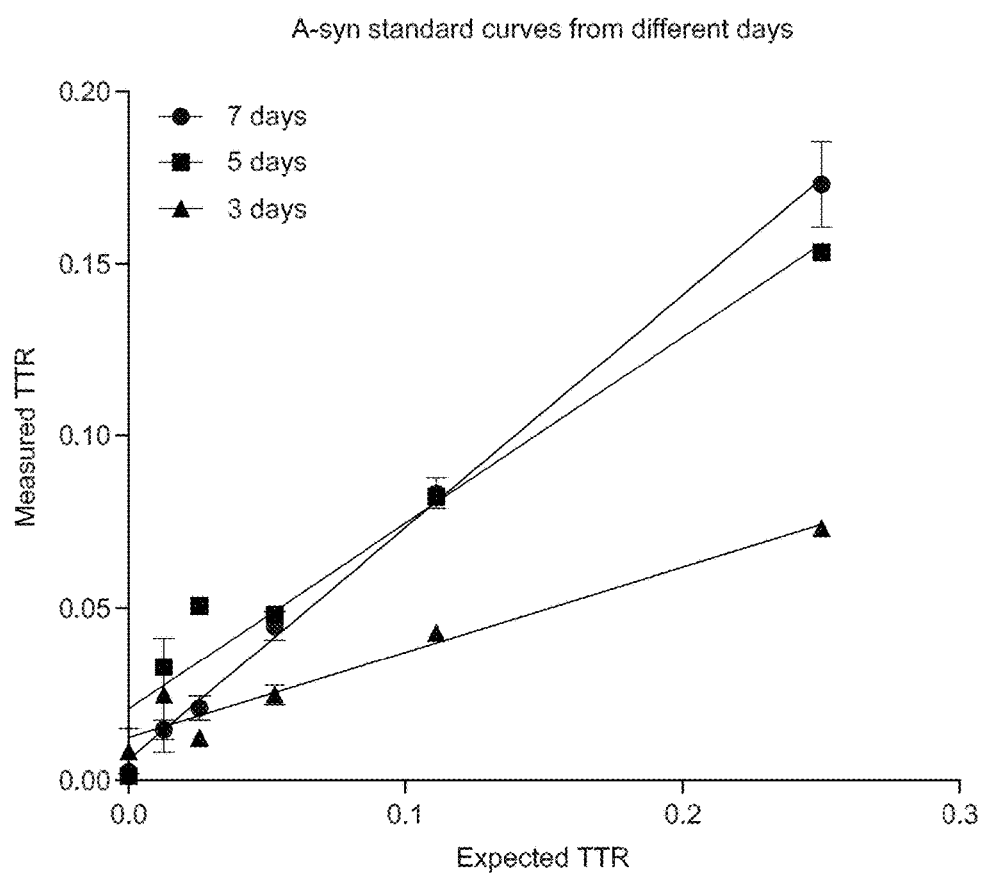
FIG. 7 shows alpha-synuclein standard curves derived from samples taken 3, 5 and 7 days after administration of the labeled moiety.
Figure 8:
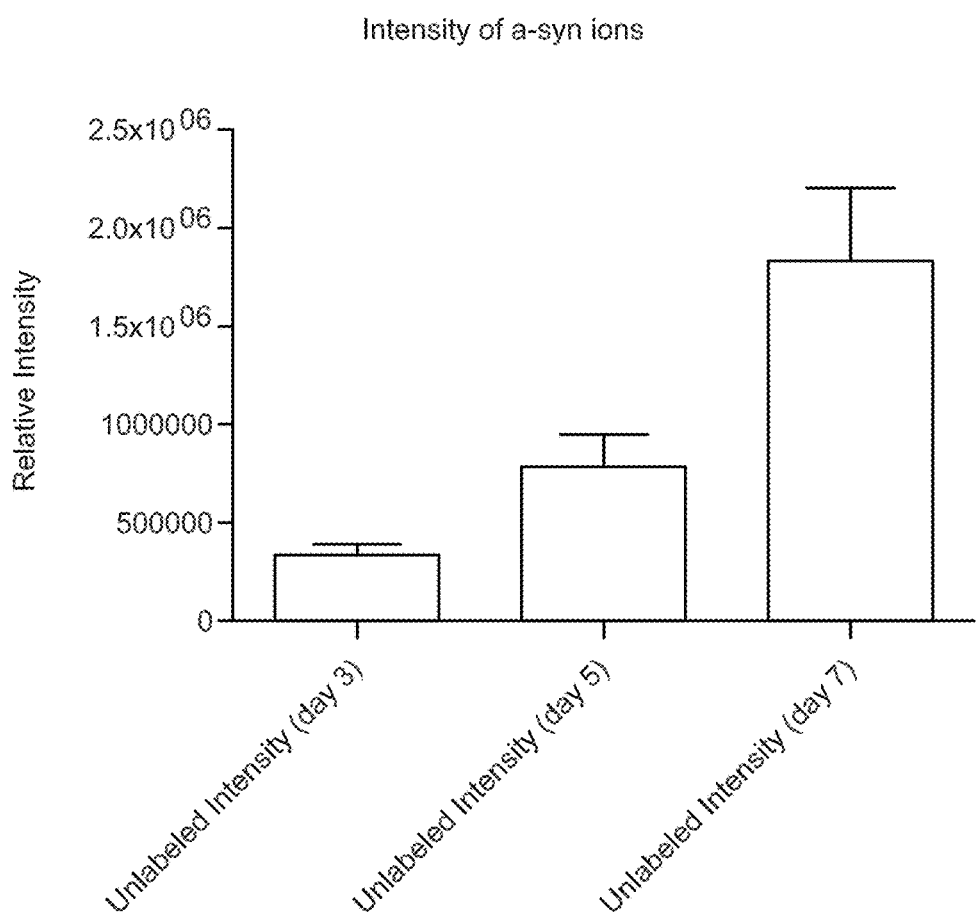
FIG. 8 shows the relative intensity of alpha-synuclein ions derived from samples taken 3, 5 and 7 days after administration of the labeled moiety.
Figure 9:
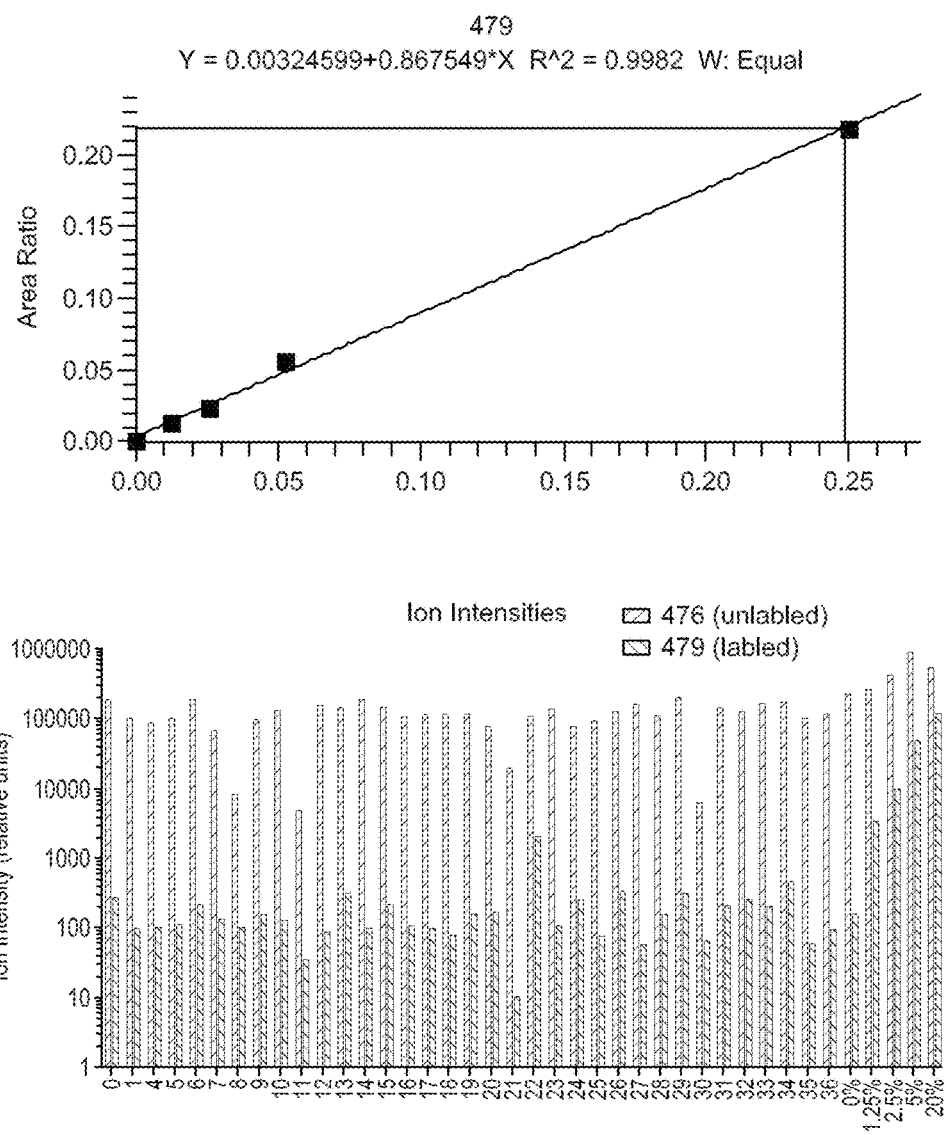
FIG. 9 shows the relative ion intensity of alpha-synuclein measured in labeled and unlabeled samples.
Figure 10:
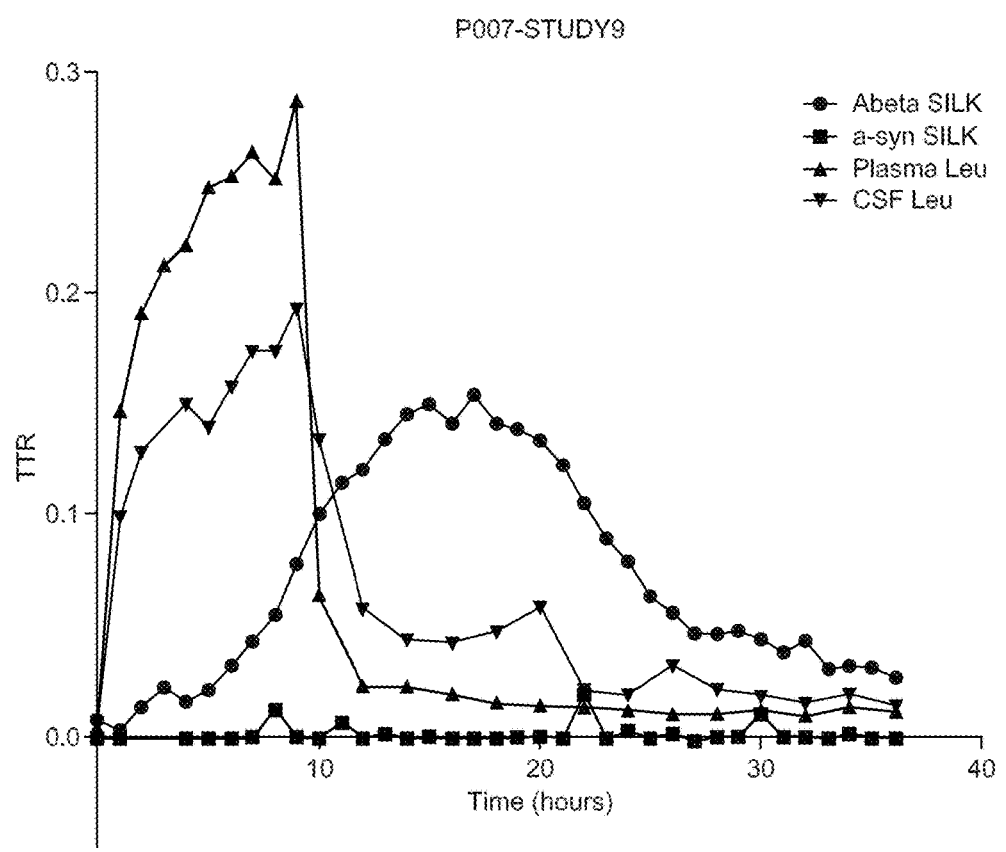
FIG. 10 shows the levels of amyloid beta protein and alpha-synuclein detected by the SILK assay over 36 hours post administration of the labeled moiety.

The present invention is based, in part, on the discovery that stable isotope labeling of biomolecules leads to small differences in molecular weight of the biomolecules, but does not alter the physical or chemical properties of the biomolecules. Using the techniques provided herein, analysis of biomolecules can be used to diagnose and/or treat a subject having or at risk of developing a neurological or neurodegenerative disorder. Accordingly, the present invention provides methods and kits useful for measuring the metabolism of alpha-synuclein in a subject.

The invention also provides a method to assess whether a therapeutic agent affects the production or clearance rate of alpha-synuclein in the subject. Accordingly, the method may be used to determine the optimal doses and/or optimal dosing regimens of the therapeutic agent. Additionally, the method may be used to determine which subjects respond better to a particular therapeutic agent. For example, subjects with increased production of alpha-synuclein may respond better to one therapeutic agent, whereas subjects with decreased clearance of alpha-synuclein may respond better to another therapeutic agent. Alternatively, subjects with one particular genotype may respond better to a particular therapeutic agent than those with a different genotype. Finally, by allowing isoform specific quantitation, the method may be used to determine whether a therapeutic agent can modulate the production of an alpha-synuclein by switching production of one isoform to another isoform.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject. In addition, the term "subject" may refer to a culture of cells, where the methods of the invention are performed in vitro to assess, for example, efficacy of a therapeutic agent.

As used herein, the terms "sample" and "biological sample" refer to any sample suitable for the methods provided by the present invention. A sample of cells used in the present method can be obtained from tissue samples or bodily fluid from a subject, or tissue obtained by a biopsy procedure (e.g., a needle biopsy) or a surgical procedure. In certain embodiments, the biological sample of the present invention is a sample of bodily fluid, e.g., cerebral spinal fluid (CSF), blood, plasma, urine, saliva, and tears.

The term "antibody" as used in this invention is meant to include intact molecules of polyclonal or monoclonal antibodies, as well as fragments thereof, such as Fab and F(ab')$_2$, Fv and SCA fragments which are capable of binding an epitopic determinant. The term "specifically binds" or "specifically interacts," when used in reference to an antibody means that an interaction of the antibody and a particular epitope has a dissociation constant of at least about $1\times10^{-6}$, generally at least about $1\times10^{-7}$, usually at least about $1\times10^{-8}$, and particularly at least about $1\times10^{-9}$ or $1\times10^{-10}$ or less.

As used herein the term "alpha-synuclein related disease or disorder" refers to any disease or disorder in which circulating levels or production of alpha-synuclein or alpha-synuclein metabolism is changed from normal. This change can be an increase or decrease in alpha-synuclein levels or metabolism compared to normal.

As disclosed herein, stable isotope labeling of alpha-synuclein leads to small differences in molecular weight of alpha-synuclein, but does not alter the general physical or chemical properties of alpha-synuclein. Thus, alpha-synuclein will bind to antibodies and elute off a liquid chromatography column in an identical fashion. Only sensitive instruments, such as mass spectrometers, provide the ability to measure the small differences in weight between labeled and unlabeled alpha-synuclein.

Several different moieties may be used to label alpha-synuclein. Generally speaking, the two types of labeling moieties utilized in the method of the invention are radioactive isotopes and non-radioactive (stable) isotopes. In one embodiment, non-radioactive isotopes may be used and measured by mass spectrometry. Preferred stable isotopes include deuterium ($^2$H), $^{13}$C, $^{15}$N, $^{17\,or\,18}$O, and $^{33,\,34,\,or\,36}$S, but it is recognized that a number of other stable isotopes that change the mass of an atom by more or less neutrons than is seen in the prevalent native form would also be effective. A suitable label generally will change the mass of alpha-synuclein such that it can be detected in a mass spectrometer. Alternatively, a radioactive isotope may be used, and the labeled alpha-synuclein may be measured with a scintillation counter (or via nuclear scintigraphy) as well as by a mass spectrometer. One or more labeled moieties may be used simultaneously or in sequence.

Thus, in one embodiment, when the method is employed to measure the metabolism of alpha-synuclein, the labeled moiety typically will be an amino acid. Those of skill in the art will appreciate that several amino acids may be used to provide the label of alpha-synuclein. Generally, the choice of amino acid is based on a variety of factors such as: (1) The amino acid generally is present in at least one residue of alpha-synuclein. (2) The amino acid is generally able to quickly reach the site of protein production and rapidly equilibrate across the blood-brain barrier or other tissue or cellular barriers. (3) The amino acid label generally does not influence the metabolism of the protein of interest (e.g., very large doses of leucine may affect muscle metabolism). And (4) availability of the desired amino acid (i.e., some amino acids are much more expensive or harder to manufacture than others).

In one embodiment, the amino acid is an essential amino acid (not produced by the body), so that a higher percent of labeling may be achieved. In another embodiment, the amino acid is a non-essential amino acid. Exemplary amino acids include, but are not limited to, leucine, isoleucine, and phenylalanine. As such, in one embodiment, the labeled amino acid is one or more of a $^{15}$N-labeled amino acid, a $^{13}C_x$-labeled phenylalanine, where x=1 to 9, a $^{13}C_x$-labeled isoleucine, where x=1 to 6. For example, $^{13}C_6$-phenylalanine, which contains six $^{13}$C atoms, may be used to label alpha-synuclein. In another embodiment, $^{13}C_6$-leucine may be used to label alpha-synuclein.

There are numerous commercial sources of labeled amino acids, both non-radioactive isotopes and radioactive isotopes. Generally, the labeled amino acids may be produced either biologically or synthetically. Biologically produced amino acids may be obtained from an organism (e.g., kelp/seaweed) grown in an enriched mixture of $^{13}$C, $^{15}$N, or another isotope that is incorporated into amino acids as the organism produces proteins. The amino acids are then separated and purified. Alternatively, amino acids may be made with known synthetic chemical processes.

In one embodiment, when the method is employed to measure the metabolism of alpha-synuclein, the labeled moiety typically will be labeled water. In one aspect, the labeled water is deuterated water ($^2$H$_2$O). In another aspect, the labeled water is oxygen 18 water (H$_2$$^{18}$O). In a further aspect, the labeled water is a molecule similar to deuterated water or oxygen 18 water.

The labeled moiety (e.g., labeled amino acid) may be administered to a subject by several methods. Suitable routes of administration include intravenously, intra-arterially, subcutaneously, intraperitoneally, intramuscularly, or orally. In one embodiment, the labeled moiety may be administered by intravenous infusion. In another embodiment, the labeled moiety may be orally ingested.

The labeled moiety may be administered slowly over a period of time, as a large single dose depending upon the type of analysis chosen (e.g., steady state or bolus/chase), or slowly over a period of time after an initial bolus dose. To achieve steady-state levels of the labeled alpha-synuclein, the labeling time generally should be of sufficient duration so that the labeled alpha-synuclein may be reliably quantified. In one embodiment, the labeled moiety is administered as a single oral dose. In another embodiment, the labeled moiety is administered for a period of time ranging from about one hour to about 36 hours. In another embodiment, the labeled moiety is administered for a period of time ranging from about 6 hours to about 12 hours. In yet another embodiment, the labeled moiety is administered for a period of time ranging from about 9 hours to about 12 hours. In yet another embodiment, the labeled moiety is administered for a period of time ranging from about 9 hours to about 24 hours. The rate of administration of the labeled moiety may range from about 0.5 mg/kg/hr to about 5 mg/kg/hr. In one embodiment, the rate of administration of labeled leucine is from about 1 mg/kg/hr to about 3 mg/kg/hr. In another embodiment, the rate of administration of labeled leucine is from 1.8 mg/kg/hr to about 2.5 mg/kg/hr. In another embodiment, the labeled leucine may be administered as a bolus of between about 50 and about 500 mg/kg body weight of the subject, between about 50 and about 300 mg/kg body weight of the subject, or between about 100 and about 300 mg/kg body weight of the subject. In yet another embodiment, the labeled leucine may be administered as a bolus of about 200 mg/kg body weight of the subject. In an alternate embodiment, the labeled leucine may be administered intravenously as detailed above after an initial bolus of between about 0.5 to about 10 mg/kg, between about 1 to about 4 mg/kg, or about 2 mg/kg body weight of the subject. In another embodiment the water will be administered daily over 1-7 days.

Those of skill in the art will appreciate that the amount (or dose) of the labeled moiety can and will vary. Generally, the amount is dependent on (and estimated by) the following factors: (1) The type of analysis desired. For example, to achieve a steady state of about 15% labeled leucine in plasma requires about 2 mg/kg/hr over about 9 hr after an initial bolus of 3 mg/kg over 10 min. In contrast, if no steady state is required, a large bolus of labeled moiety (e.g., 1 or 5 grams of labeled leucine) may be given initially. (2) The rate of metabolism of alpha-synuclein. For example, if alpha-synuclein is being produced rapidly, then less labeling time may be needed and less label may be needed—perhaps as little as 0.5 mg/kg over 1 hour. However, most proteins have half-lives of hours to days and, so more likely, a continuous infusion for 9, 12 or 24 hours may be used at 0.5 mg/kg to 4 mg/kg. And (3) the sensitivity of detection of the label. For example, as the sensitivity of label detection increases, the amount of label that is needed may decrease.

It should be understood that more than one labeled moiety may be used in a single subject. This would allow multiple labeling of alpha-synuclein and may provide information on the production or clearance of alpha-synuclein at different times. For example, a first label may be given to subject over an initial time period, followed by a pharmacologic agent (drug), and then a second label may be administered. In general, analysis of the samples obtained from the subject would provide a measurement of metabolism of alpha-synuclein before AND after drug administration, directly measuring the pharmacodynamic effect of the drug in the same subject. Alternatively, multiple labels may be used at the same time to increase labeling of alpha-synuclein.

The method of the invention provides that a sample be obtained from the subject such that the metabolism of alpha-synuclein can be determined. In one embodiment, the sample is a body fluid. Suitable body fluids include, but are not limited to, cerebral spinal fluid (CSF), blood plasma, blood serum, urine, saliva, perspiration, and tears. In another embodiment, the sample is a tissue sample, such as a sample of tissue from the central nervous system (CNS). The sample generally will be collected using standard procedures well known to those of skill in the art.

In one embodiment, the sample is a CNS sample, which includes, but is not limited to, tissue from the central nervous system, which comprises brain tissue and spinal cord tissue.

In one embodiment of the invention, the CNS sample may be taken from brain tissue, including, but not limited to, tissue from the forebrain (e.g., cerebral cortex, basal ganglia, hippocampus), the interbrain (e.g., thalamus, hypothalamus, subthalamus), the midbrain (e.g., tectum, tegmentum), or the hindbrain (e.g., pons, cerebellum, medulla oblongata). In another embodiment, the CNS sample may be collected from spinal cord tissue. In still other embodiments, CNS samples from more than one CNS region may be taken. Accordingly, the metabolism of alpha-synuclein may be measured in different CNS samples, e.g., in the cortex and the hippocampus, simultaneously.

CNS samples may be obtained by known techniques. For instance, brain tissue or spinal cord tissue may be obtained via dissection or resection. Alternatively, CNS samples may be obtained using laser microdissection. The subject may or may not have to be sacrificed to obtain the sample, depending on the CNS sample desired and the subject utilized.

In one embodiment, the sample is obtained from the subject at a single predetermined time point, for example, within an hour of labeling. In general, for proteins with fast metabolism, samples obtained during the first 12-18 hours after the start of administration of the labeled moiety may be used to determine the rate of production of alpha-synuclein, and samples taken during 24-36 hrs after the start of administration of the labeled moiety may be used to determine the clearance rate of alpha-synuclein. In general, for proteins with slow metabolism, samples obtained during the first 1-4 days after the start of administration of the labeled moiety may be used to determine the rate of production of alpha-synuclein, and samples taken during 4-14 days after the start of administration of the labeled moiety may be used to determine the clearance rate of alpha-synuclein. In another embodiment, the sample is obtained from the subject hourly from 0 to 12 hours, 0 to 24 hours, or 0 to 36 hours. In yet another embodiment, samples may be taken from an hour to days or even weeks apart depending upon the production and clearance rates of alpha-synuclein.

Those of skill in the art will appreciate that the labeled moiety should be administered in a timely fashion which will allow observation of incorporation of the labeled moiety into alpha-synuclein. The labeling of alpha-synuclein will take place as the protein is synthesized inside the cell. But the incorporation of the label into alpha-synuclein is only measured once the protein has exited the cell and entered the cerebrospinal fluid or the blood stream. If the protein undergoes complex processing in order to exit the cell, the time from synthesis until appearance in the bodily fluid could be significant. Thus if it takes 24-48 hours for alpha-synuclein to show up in CSF, administration of label may have to occur 24-48 hours before the start of CSF sampling. Alternatively, if it takes 48-72 hours for alpha-synuclein to show up in CSF, administration of label may have to occur 48-72 hours before the start of CSF sampling. Further, if it takes 3 days to one week for alpha-synuclein to show up in CSF, administration of label may have to occur 3 days to one week before the start of CSF sampling.

It should be understood that if samples at different timepoints are desired, more than one subject may be used. For instance, one subject may be used for a baseline sample, another subject for a time-point of one hour post administration of the labeled moiety, another subject for a time-point six hours post administration of the labeled moiety.

Accordingly, the present invention provides that detection of the amount of labeled alpha-synuclein and the amount of unlabeled alpha-synuclein in the sample may be used to determine the ratio of labeled alpha-synuclein to unlabeled alpha-synuclein, which in turn, may be used to estimate the production and clearance rates of alpha-synuclein in the subject. Exemplary means for detecting differences in mass between the labeled and unlabeled alpha-synuclein include, but are not limited to, liquid chromatography mass spectrometry, gas chromatography mass spectrometry, MALDI-TOF mass spectrometry, and tandem mass spectrometry.

However, prior to detecting the ratio of labeled alpha-synuclein to unlabeled alpha-synuclein, it may be desirable to isolate and/or separate alpha-synuclein from other biomolecules in the sample. Thus, in one embodiment, immunoprecipitation may be used to isolate and purify alpha-synuclein before it is analyzed. In another embodiment, alpha-synuclein may be isolated or purified by affinity chromatography or immunoaffinity chromatography. Alternatively, mass spectrometers having chromatography setups may be used to separate biomolecules without immunoprecipitation, and then alpha-synuclein may be measured directly. In an exemplary embodiment, alpha-synuclein may be immunoprecipitated and then analyzed by a liquid chromatography system interfaced with a tandem MS unit equipped with an electrospray ionization source (LC-ESI-tandem MS).

In another aspect, the invention provides that the metabolism of multiple biomolecules in the same sample may be measured simultaneously. That is, both the amount of unlabeled and labeled biomolecule may be detected and measured separately or at the same time for multiple biomolecules. As such, the invention provides a useful method for screening changes in production and clearance of one or more biomolecules on a large scale (i.e., proteomics/metabolomics) and provides a sensitive means to detect and measure biomolecules involved in the underlying pathophysiology. In one aspect, the invention also provides a means to measure multiple types of biomolecules. In this context, for example, a protein and a lipid may be measured simultaneously or sequentially. For example, both alpha-synuclein and Aβ could be isolated from a CSF sample and the production and clearance of the two individual proteins be determined in the same subject.

Once the amount of labeled and unlabeled alpha-synuclein has been detected in a sample, the ratio or percent of labeled alpha-synuclein to unlabeled alpha-synuclein may be determined by dividing the amount of labeled alpha-synuclein with the amount of unlabeled alpha-synuclein. If a mass spectrometer is used for detection of alpha-synuclein, the ratio would be calculated by dividing the ion intensity of labeled alpha-synuclein with the ion intensity of unlabeled alpha-synuclein.

The invention allows measurement of the labeled and unlabeled protein at the same time, so that the ratio of labeled to unlabeled protein, as well as other calculations, may be made. As measurements of labeling ratios are combined over different sampling times after infusion of the stable isotope, the data can be combined to form a metabolic profile. Those of skill in the art will be familiar with the first order kinetic models of labeling that may be used with the method of the invention. For example, the fractional synthesis rate (FSR) may be calculated. The FSR equals the initial rate of increase of labeled to unlabeled protein divided by the precursor enrichment. Likewise, the fractional clearance rate (FCR) may be calculated. In addition, other parameters, such as fractional turnover rate (FTR), lag time, and isotopic tracer steady state, may be determined and used as measurements of the protein's metabolism and physiology. Also, modeling may be performed on the data to fit multiple compartment models to estimate transfer between compartments. Of course, the type of mathematical modeling chosen will depend on the individual synthesis and clearance parameters (e.g., one-pool, multiple pools, steady state, non-steady-state, compartmental modeling, etc.). As used herein, "steady state" refers to a state during which there is insignificant change in the measured parameter over a specified period of time.

Stable isotope kinetic labeling (SILK) methodology has been shown to detect metabolic incorporation of stable (non-radioactive) isotopes into newly synthesized proteins in the cerebrospinal fluid of living subject. For detailed information regarding SILK, see U.S. Pub. Nos. 2008/0145941 and 2009/0142766, and International PCT Pub. No. WO 2006/107814, the entire content of each of which is incorporated herein by reference). SILK makes it possible to measure the production and clearance rates of proteins in the central nervous system. Thus far, this methodology has been applied to measuring the production and clearance of the amyloid beta protein (Aβ) implicated in Alzheimer's disease (AD).

However, until now, the current version of the SILK assay measures only the metabolism of Aβ. In the data demonstrated here we show that the SILK method can also be applied to alpha-synuclein. This assay is distinct in the use of an antibody that specifically binds to alpha-synuclein for isolation of alpha-synuclein from the biological fluid and in the selection of alpha-synuclein specific peptides for monitoring of stable isotope incorporation into alpha-synuclein.

Accordingly, the production of protein is typically based upon the rate of increase of the labeled/unlabeled protein ratio over time (i.e., the slope, the exponential fit curve, or a compartmental model fit defines the rate of protein production). For these calculations, a minimum of one sample is typically required (one could estimate the baseline label), two are preferred, and multiple samples are more preferred to calculate an accurate curve of the uptake of the label into the protein (i.e., the production rate). If multiple samples are used or preferred, the samples need not be taken from the same subject. For instance, proteins may be labeled in five different subjects at time point zero, and then a single sample taken from each subject at a different time point post-labeling.

Conversely, after the administration of labeled amino acid is terminated, the rate of decrease of the ratio of labeled to unlabeled protein typically reflects the clearance rate of that protein. For these calculations, a minimum of one sample is typically required (one could estimate the baseline label), two are preferred, and multiple samples are more preferred to calculate an accurate curve of the decrease of the label from the protein over time (i.e., the clearance rate). If multiple samples are used or preferred, the samples need not be taken from the same subject. For instance, proteins may be labeled in five different subjects at time point zero, and then a single sample taken from each subject at a different time point post-labeling. The amount of labeled protein in a CNS sample at a given time reflects the production rate or the clearance rate (i.e., removal or destruction) and is usually expressed as percent per hour or the mass/time (e.g., mg/hr) of the protein in the subject.

The method of the invention may be used to diagnose or monitor the progression of a neurological or neurodegenerative disease by measuring the in vivo metabolism of alpha-synuclein in a subject. Additionally, the methods of the invention may be used to monitor the treatment of a neurological or neurodegenerative disease by measuring the in vivo metabolism of alpha-synuclein in a subject. The metabolism of alpha-synuclein may be linked to a neurological or neurodegenerative disease such that any increase or decrease may be indicative of the presence or progression of the disease. Thus, the metabolism of alpha-synuclein may be compared to the metabolism of alpha-synuclein in a corresponding normal sample, to the metabolism of alpha-synuclein in a subject of known neurological or neurodegenerative disease state, to the metabolism of alpha-synuclein from the same subject determined at an earlier time, or any combination thereof.

In addition, such methods may help identify an individual as having a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the disease.

As used herein a "corresponding normal sample" refers to a sample from the same organ and/or of the same type as the sample being examined. In one aspect, the corresponding normal sample comprises a sample of cells obtained from a healthy individual. Such a corresponding normal sample can, but need not be, from an individual that is age-matched and/or of the same sex as the individual providing the sample being examined. In another aspect, the corresponding normal sample comprises a sample of cells obtained from an otherwise healthy portion of tissue of the subject from which the sample being tested is obtained.

Reference to the metabolism of alpha-synuclein in a subject of known neurological or neurodegenerative disease state includes a predetermined metabolism of alpha-synuclein linked to a neurological or neurodegenerative disease. Thus, the metabolism may be compared to a known metabolism of alpha-synuclein obtained from a sample of a single individual or may be from an established cell line of the same type as that of the subject. In one aspect, the established cell line can be one of a panel of such cell lines, wherein the panel can include different cell lines of the same type of disease and/or different cell lines of different diseases associated with alpha-synuclein. Such a panel of cell lines can be useful, for example, to practice the present method when only a small number of cells can be obtained from the subject to be treated, thus providing a surrogate sample of the subject's cells, and also can be useful to include as control samples in practicing the present methods.

Exemplary neurological or neurodegenerative diseases that may be linked to the metabolism of alpha-synuclein include, but are not limited to, Alzheimer's Disease, Parkinson's Disease, stroke, frontal temporal dementias (FTD$_s$), aging-related disorders and dementias, Lewy Body Disease, Traumatic Brain Injury (TBI), and Amyotrophic Lateral Sclerosis (ALS or Lou Gehrig's Disease). It is also envisioned that the method of the invention may be used to study the normal physiology, metabolism, and function of the CNS.

In another aspect, the present invention provides a method for assessing whether a therapeutic agent used to treat a neurological or neurodegenerative disease affects the metabolism of alpha-synuclein in the subject. For example, the metabolism of alpha-synuclein may be measured to determine if a given therapeutic agent results in an increase, or a decrease in the production or clearance of alpha-synuclein. In one embodiment, the method is performed in vivo, as herein described. In another embodiment, the method is performed in vitro utilizing a culture of cells, where the culture of cells is the "subject" in the methods described herein. Accordingly, use of the methods provided herein will allow those of skill in the art to accurately determine the degree of change in the metabolism of alpha-synuclein, and correlate these measurements with the clinical outcome of the disease modifying treatment. Results from this aspect of the invention, therefore, may help determine the optimal doses and frequency of doses of a therapeutic agent, may assist in the decision-making regarding the design of clinical trials, and may ultimately accelerate validation of effective therapeutic agents for the treatment of neurological or neurodegenerative diseases.

Thus, the method of the invention may be used to predict which subjects will respond to a particular therapeutic agent. For example, subjects with increased metabolism of alpha-synuclein may respond to a particular therapeutic agent differently than subjects with decreased metabolism of alpha-synuclein. In particular, results from the method may be used to select the appropriate treatment (e.g., an agent that blocks the production of alpha-synuclein or an agent that increases the clearance alpha-synuclein) for a particular subject. Similarly, results from the method may be used to select the appropriate treatment for a subject having a particular genotype.

The method for predicting which subjects will respond to a particular therapeutic agent include administering a therapeutic agent and a labeled moiety to the subject, wherein the labeled moiety is incorporated into alpha-synuclein as it is produced in the subject. In one embodiment, the therapeutic agent may be administered to the subject prior to the administration of the labeled moiety. In another embodiment, the labeled moiety may be administered to the subject prior to the administration of the therapeutic agent. The period of time between the administration of each may be several minutes, an hour, several hours, or many hours. In still another embodiment, the therapeutic agent and the labeled moiety may be administered simultaneously. The method further includes collecting at least one biological sample, which includes labeled and unlabeled alpha-synuclein, determining a ratio of the labeled alpha-synuclein and unlabeled alpha-synuclein in the sample, and calculating the metabolism of alpha-synuclein in the subject. Thereafter, a comparison of the calculated metabolism to a control value will determine whether the therapeutic agent alters the metabolism (e.g., by altering the rate of production or the rate of clearance) of alpha-synuclein in the subject.

Those of skill in the art will appreciate that the therapeutic agent can and will vary depending upon the neurological or neurodegenerative disease or disorder to be treated. Non-limiting examples of suitable therapeutic agents include small molecule inhibitors of alpha-synuclein production, humanized antibodies against alpha-synuclein, alpha-synuclein CNS clearance activators, sirtuin 2 inhibitors, proteosome inhibitors, small molecule inhibitors of alpha-synuclein polymerization.

Other suitable AD therapeutic agents include cholesterylester transfer protein (CETP) inhibitors, metalloprotease inhibitors, cholinesterase inhibitors, NMDA receptor antagonists, hormones, neuroprotective agents, Aβ production inhibitors such as inhibitors and modulators of gamma and beta secretases, anti-Aβ antibodies, anti-Tau antibodies, and cell death inhibitors. Many of the above mentioned therapeutic agents may also affect the in vivo metabolism of other proteins implicated in neurodegenerative disorders.

The therapeutic agent may be administered to the subject in accord with known methods. Typically, the therapeutic agent will be administered orally, but other routes of administration such as parenteral or topical may also be used. The amount of therapeutic agent that is administered to the subject can and will vary depending upon the type of agent, the subject, and the particular mode of administration. Those skilled in the art will appreciate that dosages may be determined with guidance from Goodman & Goldman's The Pharmacological Basis of Therapeutics, Tenth Edition (2001), Appendix II, pp. 475-493, and the Physicians' Desk Reference.

In another aspect, the invention provides a kit for performing the methods of the invention. In one embodiment, a kit is provided for diagnosing and/or monitoring the progression or treatment of a neurological or neurodegenerative disease in a subject. The kit includes one or more labeled moieties (e.g., labeled amino acids) and a means for administering the one or more amino acids to the subject. The kit may further include a means for obtaining a biological sample at regular time intervals from the subject. In certain embodiments, the kit will also include instructions for detecting and determining the ratio of labeled to unlabeled alpha-synuclein over time and for calculating the metabolism of alpha-synuclein. In one embodiment, the instructions will disclose methods for comparing the calculated concentration to certain standards and/or controls as disclosed herein.

In another embodiment, the kit of the invention provides a compartmentalized carrier including one or more containers containing the labeled moiety and the various means for performing the methods of the invention.

In this embodiment of the invention, we demonstrate the feasibility of a stable isotope labeling kinetics (SILK) alpha-synuclein assay. FIG. 1 shows the tryptic cleavage sites in the alpha-synuclein sequence and thus a list of possible tryptic peptides originating from alpha-synuclein. Other proteases can be used instead of trypsin and will yield different cleavage patterns and different peptides. When digesting recombinant alpha-synuclein or alpha-synuclein isolated from biological sources we observed several tryptic peptides originating from alpha-synuclein. FIG. 3 shows a list of peptides that we have observed either from recombinant alpha-synuclein or from alpha-synuclein that has been isolated from CSF or other biological sources.

The following examples are provided to further illustrate the advantages and features of the present invention, but are not intended to limit the scope of the invention. While they are typical of those that might be used, other procedures, methodologies, or techniques known to those skilled in the art may alternatively be used.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Measurement of Incorporation of $^{13}C_6$ Leucine into Alpha-Synuclein Produced by Cells Tissue culture cells (SH-SY5Y) were stably transfected with a construct that leads to over-expression of alpha-synuclein. The cells were grown in media containing known ratios of $^{13}C_6$ to $^{12}C_6$ labeled leucine (tracer to tracee ratio; TTR) (TTR=0.00, 0.0127, 0.0256, 0.0526, 0.111, 0.25). Media was collected after 3, 5, and 7 days of growing in the labeled media. Alpha-synuclein was isolated from media samples by immunoprecipitation using C2N-ASMAB3. Isolated proteins were digested with trypsin and analyzed on a TSQ-Vantage triple quadruple mass spectrometer setup to monitor the labeled and unlabeled alpha-synuclein 35-43 peptide. The ratio of labeled to unlabeled alpha-synuclein was calculated for each sample. The approximate concentration of alpha-synuclein as measured by the intensity of the labeled and unlabeled alpha-synuclein increased from the initial collection to the subsequent collections as the cells grew more confluent. In addition, the ratio of labeled to unlabeled alpha-synuclein more closely matched the expected concentrations as the cells turned over the originally unlabeled alpha-synuclein and produced new alpha-synuclein using the mixture of labeled and unlabeled amino acids.

Example 2

Measurement of Incorporation of $^{13}C_6$ Leucine into Alpha-Synuclein Produced by Humans A human volunteer was administered $^{13}C_6$ leucine for 9 hours and had CSF samples taken every hour for 36 hours starting at the time of leucine infusion. Alpha-synuclein was isolated from the CSF samples as well as samples from one $^{13}C_6$ leucine alpha-synuclein standard curve by immunoprecipitation and digested with trypsin. Incorporation of $^{13}C_6$ leucine into the 35-43 peptide was analyzed for each sample by mass spectrometer.

Although the invention has been described with reference to the above examples, it will be understood that modifications and variations are encompassed within the spirit and scope of the invention. Accordingly, the invention is limited only by the following claims.

The invention claimed is:

1. A method comprising:
   a) administering a labeled moiety to a subject suspected of having Alzheimer's disease (AD), wherein the labeled moiety incorporates into alpha-synuclein thereby producing labeled alpha-synuclein;
   b) obtaining a biological sample from the subject;
   c) determining metabolic incorporation of the labeled moiety into alpha-synuclein in the biological sample, wherein determining the metabolic incorporation comprises measuring the level of labeled alpha-synuclein and unlabeled alpha-synuclein in a polypeptide selected from the group consisting of SEQ ID NOs: 4-13 in the biological sample via a stable isotope labeling kinetics (SILK) assay and determining the ratio of labeled alpha-synuclein to unlabeled alpha-syuclein; and
   d) comparing the metabolic incorporation of (c) with that of a corresponding normal sample.

2. The method of claim 1, further comprising administering a therapeutic agent to the subject.

3. The method of claim 1, wherein the labeled moiety is a labeled amino acid or labeled water.

4. The method of claim 3, wherein the amino acid is labeled with a radioisotope or a non-radio-labeled isotope.

5. The method of claim 4, wherein the non-radio labeled isotope is selected from the group consisting of: 2H, 13C, 15N, 17or 18O and 33, 34 or 36S.

6. The method of claim 3, wherein the amino acid is selected from the group consisting of leucine, isoleucine and phenylalanine.

7. The method of claim 6, wherein the labeled amino acid is selected from the group consisting of one or more of: 15Nx labeled leucine, wherein x=1-6; 13Cx labeled phenylalanine, wherein x=1-9 and 13Cx labeled isoleucine, wherein x=1-6.

8. The method of claim 1, wherein the labeled moiety is a labeled water.

9. The method of claim 8, wherein the labeled water is selected from the group consisting of deuterated water or oxygen 18 water.

10. The method of claim 1, wherein the biological sample is a bodily fluid or a tissue sample.

11. The method of claim 1, wherein the biological sample is a bodily fluid selected from the group consisting of: blood, plasma, blood serum, cerebral spinal fluid (CSF) and urine.

12. The method of claim 1, wherein the biological sample is a CNS sample selected from the group consisting of: tissue from the CNS, brain tissue, forebrain tissue, interbrain tissue, midbrain tissue, hindbrain tissue and spinal cord tissue.

* * * * *